(12) United States Patent
Karuppiah et al.

(10) Patent No.: US 11,789,841 B2
(45) Date of Patent: Oct. 17, 2023

(54) SYSTEMS AND METHODS FOR MONITOR AND ALERT FOR POLLUTANTS IN AN ENVIRONMENT OF AN INFORMATION HANDLING SYSTEM

(71) Applicant: Dell Products L.P., Round Rock, TX (US)

(72) Inventors: Kannan Karuppiah, Fremont, CA (US); Per Fremrot, Novato, CA (US); Shree Rathinasamy, Round Rock, TX (US)

(73) Assignee: Dell Products L.P., Round Rock, TX (US)

( * ) Notice: Subject to any disclaimer, the term of this patent is extended or adjusted under 35 U.S.C. 154(b) by 70 days.

(21) Appl. No.: 17/496,133

(22) Filed: Oct. 7, 2021

(65) Prior Publication Data
US 2023/0112501 A1    Apr. 13, 2023

(51) Int. Cl.
*G06F 11/30* (2006.01)
*H05K 7/20* (2006.01)
*G01N 15/10* (2006.01)
*G01N 33/00* (2006.01)

(52) U.S. Cl.
CPC ......... *G06F 11/3058* (2013.01); *G01N 15/10* (2013.01); *G01N 33/0062* (2013.01); *H05K 7/20136* (2013.01)

(58) Field of Classification Search
CPC ........ G06F 11/3058; G06F 1/206; G06F 1/20; G06F 1/3203; G01N 33/0062; G01N 15/10; H05K 7/20136; H05K 7/202; H05K 7/20836; H05K 7/20209; F24F 11/30; F24F 11/63; F24F 11/74

USPC ......... 361/600, 695, 679.48, 679.02, 679.46, 361/679.49, 688, 690, 719; 700/1, 108, 700/275, 300; 702/1, 19, 22–24, 33–35, 702/45, 57, 85, 100, 113, 117, 127, 150, 702/183–184, 189

See application file for complete search history.

(56) References Cited

U.S. PATENT DOCUMENTS

| | | | | |
|---|---|---|---|---|
| 2005/0024216 | A1* | 2/2005 | Crooks | F24F 11/49 340/606 |
| 2010/0252358 | A1* | 10/2010 | Rodrigues | G06F 1/20 181/206 |
| 2014/0016268 | A1* | 1/2014 | Tsujimura | G06F 1/20 361/695 |
| 2017/0247108 | A1* | 8/2017 | Ljubuncic | G06F 30/13 |

FOREIGN PATENT DOCUMENTS

| | | | | |
|---|---|---|---|---|
| CN | 106168018 | A | * 11/2016 | |
| CN | 210486946 | U | * 5/2020 | |
| CN | 111813187 | A | * 10/2020 | G06F 1/183 |
| EP | 2270624 | A2 | * 1/2011 | H05K 7/20745 |

* cited by examiner

*Primary Examiner* — Jeffrey P Aiello
(74) *Attorney, Agent, or Firm* — Jackson Walker L.L.P

(57) ABSTRACT

An information handling system may include a chassis configured to house components of the information handling system and an air mover assembly comprising an enclosure, an air mover within the enclosure configured to drive airflow to cool one or more components of the information handling system, and a sensor within a path of the airflow and configured to detect a presence of matter harmful to one or more components of the information handling system.

15 Claims, 3 Drawing Sheets

SYSTEMS AND METHODS FOR MONITOR AND ALERT FOR POLLUTANTS IN AN ENVIRONMENT OF AN INFORMATION HANDLING SYSTEM

TECHNICAL FIELD

The present disclosure relates in general to information handling systems, and more particularly to systems and methods for monitoring and alerting for pollutants in an environment of an information handling system.

BACKGROUND

As the value and use of information continues to increase, individuals and businesses seek additional ways to process and store information. One option available to users is information handling systems. An information handling system generally processes, compiles, stores, and/or communicates information or data for business, personal, or other purposes thereby allowing users to take advantage of the value of the information. Because technology and information handling needs and requirements vary between different users or applications, information handling systems may also vary regarding what information is handled, how the information is handled, how much information is processed, stored, or communicated, and how quickly and efficiently the information may be processed, stored, or communicated. The variations in information handling systems allow for information handling systems to be general or configured for a specific user or specific use such as financial transaction processing, airline reservations, enterprise data storage, or global communications. In addition, information handling systems may include a variety of hardware and software components that may be configured to process, store, and communicate information and may include one or more computer systems, data storage systems, and networking systems.

Data centers and cloud environments may employ multiple information handling systems and networking equipment for interconnectivity of information handling systems. The numbers of networking switches used in data centers are increasing in accordance with modern business needs. This increase may lead to increased management and maintenance of a large number of switches. With many typical data center switches having dense ports, it is often common that 20%-40% of ports are unused, particularly when a switch is first acquired, to allow for scaling up of the network. It is imperative to protect such ports from contaminants.

Switches and other information handling systems are often cooled using air mover-driven airflow that draws cool air into an enclosure, wherein such air flows proximate to heat-generating components before being exhausted from the enclosure as heated air. As switches and other information handling systems use more power, they may in turn generate more heat, requiring increased airflow. However, unfiltered airflow may lead to potential harmful effects in a data center.

For example, sulfur, nitrogen, and other gases present in a data center may cause corrosion of printed circuit boards. In addition, the presence of dust in a data center may lead to damage to components and/or reduce the ability of components to dissipate heat. Further, other environmental conditions harmful to components may include moisture, presence of minute metal shavings, and/or the presence of corrosive particles.

Damage from such environmental pollutants may lead to a decrease in lifespan of information handling system components, data loss, and/or increased calls to customer support, all of which may impose a significant financial burden.

SUMMARY

In accordance with the teachings of the present disclosure, the disadvantages and problems associated with existing approaches to avoiding contamination of information handling system components may be reduced or eliminated.

In accordance with embodiments of the present disclosure, an information handling system may include a chassis configured to house components of the information handling system and an air mover assembly comprising an enclosure, an air mover within the enclosure configured to drive airflow to cool one or more components of the information handling system, and a sensor within a path of the airflow and configured to detect a presence of matter harmful to one or more components of the information handling system.

In accordance with these and other embodiments of the present disclosure, an air mover assembly may include an enclosure, an air mover within the enclosure configured to drive airflow to cool one or more components of an information handling system comprising the air mover assembly, and a sensor within a path of the airflow and configured to detect a presence of matter harmful to one or more components of the information handling system.

In accordance with these and other embodiments of the present disclosure, a method may include housing an air mover within an enclosure of an air mover assembly, wherein the air mover is configured to drive airflow to cool one or more components of an information handling system comprising the air mover assembly and placing a sensor within a path of the airflow, wherein the sensor is configured to detect a presence of matter harmful to one or more components of the information handling system.

Technical advantages of the present disclosure may be readily apparent to one skilled in the art from the figures, description and claims included herein. The objects and advantages of the embodiments will be realized and achieved at least by the elements, features, and combinations particularly pointed out in the claims.

It is to be understood that both the foregoing general description and the following detailed description are examples and explanatory and are not restrictive of the claims set forth in this disclosure.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION

Figure 1:
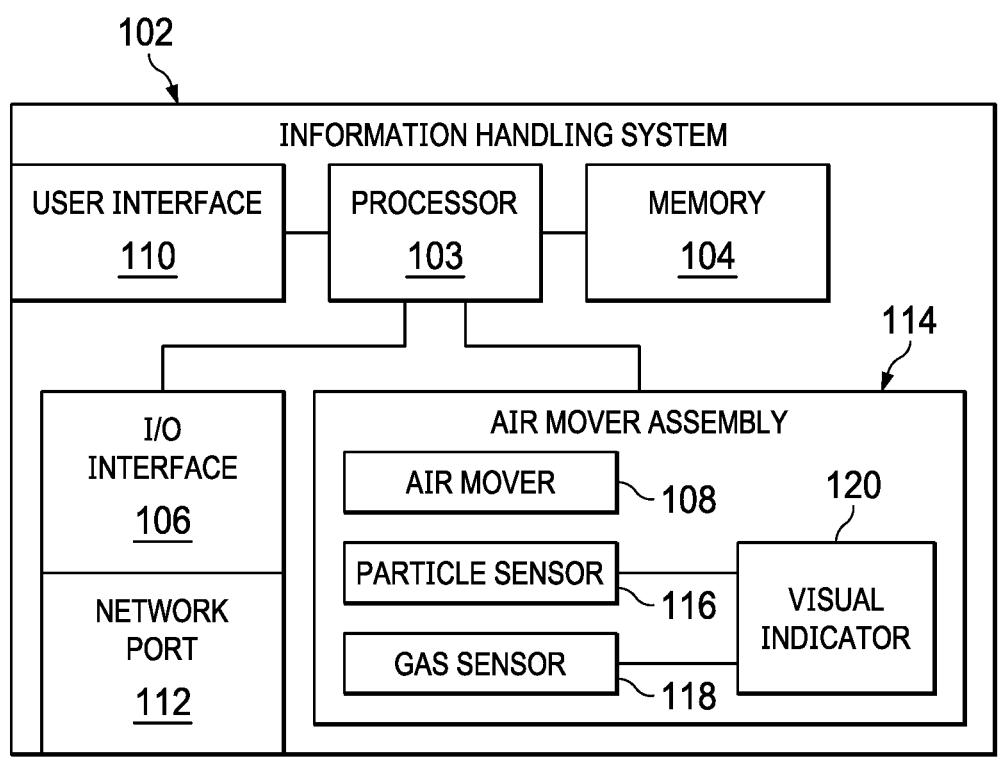
FIG. 1 illustrates a block diagram of selected components of an example information handling system, in accordance with embodiments of the present disclosure.
Figure 2A:
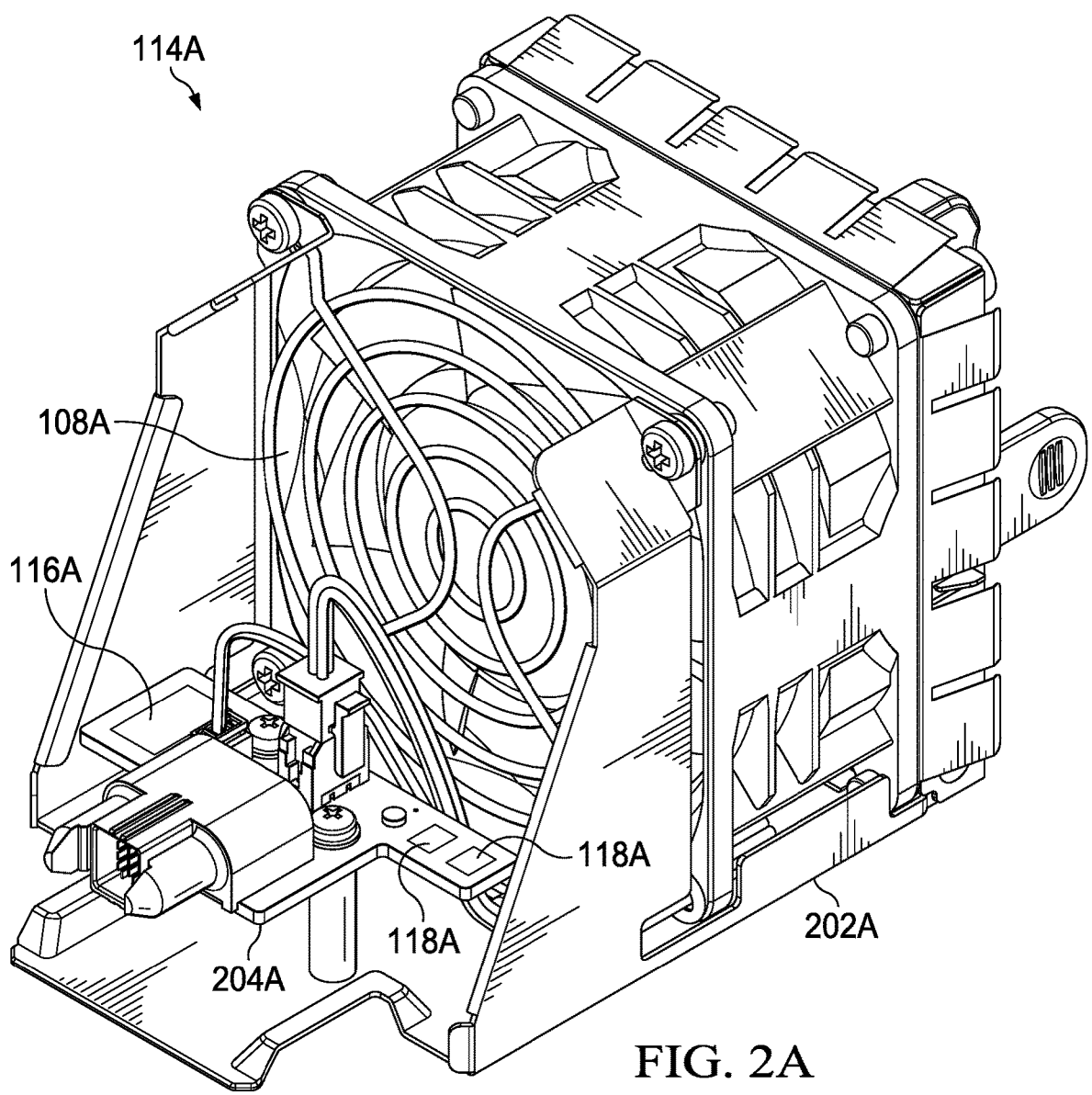
FIG. 2A illustrates a perspective view of selected components of an example air mover module, in accordance with embodiments of the present disclosure.
Figure 2B:
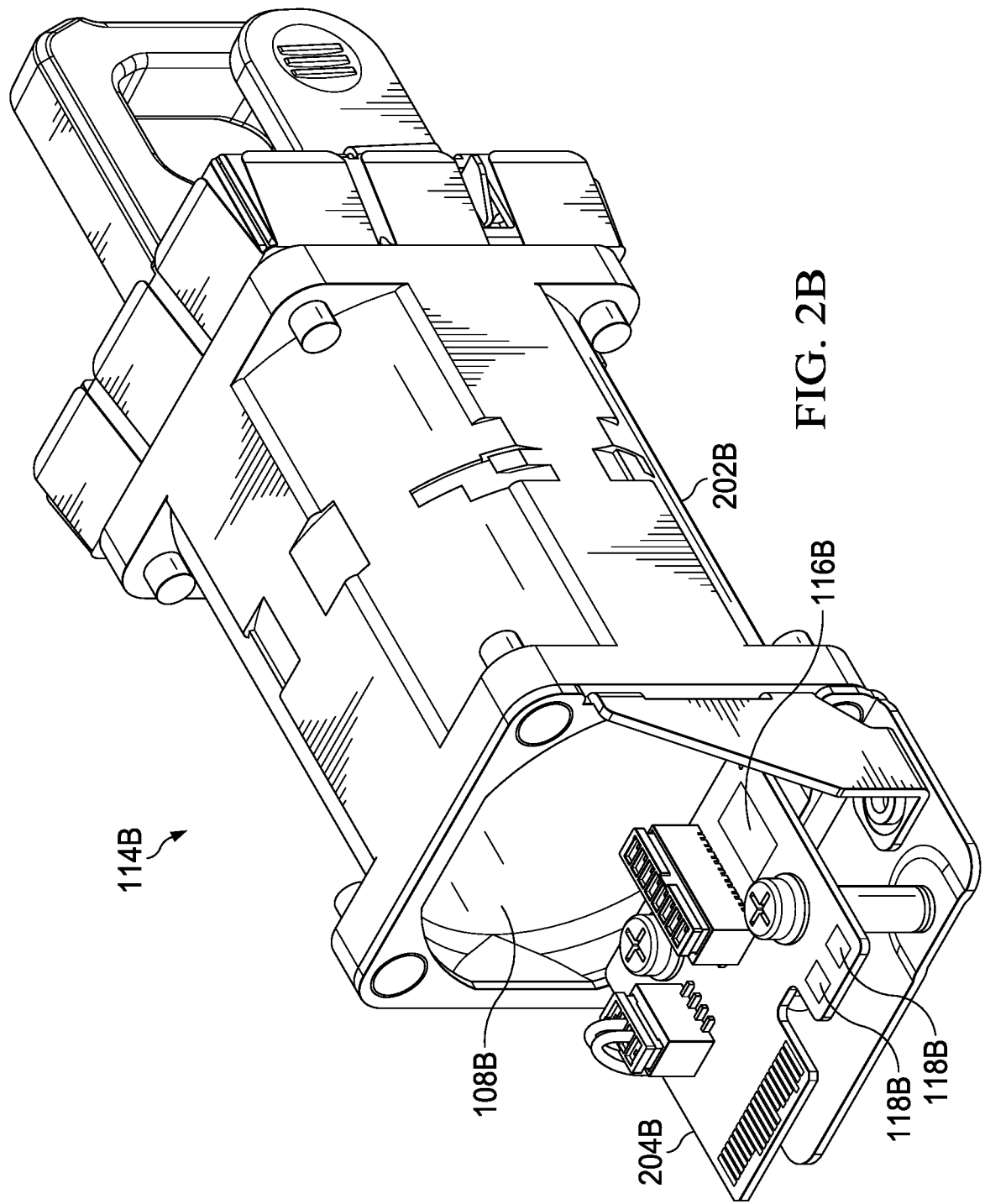
FIG. 2B illustrates a perspective view of selected components of another example air mover module, in accordance with embodiments of the present disclosure.

Preferred embodiments and their advantages are best understood by reference to FIGS. 1 through 2B, wherein like numbers are used to indicate like and corresponding parts.

For the purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, entertainment, or other purposes. For example, an information handling system may be a personal computer, a personal digital assistant (PDA), a consumer electronic device, a network storage device, or any other suitable device and may vary in size, shape, performance, functionality, and price. The information handling system may include memory, one or more processing resources such as a central processing unit ("CPU") or hardware or software control logic. Additional components of the information handling system may include one or more storage devices, one or more communications ports for communicating with external devices as well as various input/output ("I/O") devices, such as a keyboard, a mouse, and a video display. The information handling system may also include one or more buses operable to transmit communication between the various hardware components.

For the purposes of this disclosure, computer-readable media may include any instrumentality or aggregation of instrumentalities that may retain data and/or instructions for a period of time. Computer-readable media may include, without limitation, storage media such as a direct access storage device (e.g., a hard disk drive or floppy disk), a sequential access storage device (e.g., a tape disk drive), compact disk, CD-ROM, DVD, random access memory (RAM), read-only memory (ROM), electrically erasable programmable read-only memory (EEPROM), and/or flash memory; as well as communications media such as wires, optical fibers, microwaves, radio waves, and other electromagnetic and/or optical carriers; and/or any combination of the foregoing.

For the purposes of this disclosure, information handling resources may broadly refer to any component system, device or apparatus of an information handling system, including without limitation processors, service processors, basic input/output systems (BIOSs), buses, memories, I/O devices and/or interfaces, storage resources, network interfaces, motherboards, and/or any other components and/or elements of an information handling system.

FIG. 1 illustrates a block diagram of selected components of an example information handling system 102, in accordance with embodiments of the present disclosure. In some embodiments, information handling system 102 may be a personal computer (e.g., a desktop computer or a portable computer). In other embodiments, information handling system 102 may comprise a storage server for archiving data. In yet other embodiments, information handling system 102 may comprise a server. In further embodiments, information handling system 102 may comprise a network switch.

As depicted in FIG. 1, information handling system 102 may include a processor 103, a memory 104 communicatively coupled to processor 103, an input/output (I/O) interface 106 communicatively coupled to processor 103, a user interface 110 communicatively coupled to processor 103, a network port 112 communicatively coupled to I/O interface 106, and an air mover assembly 114 communicatively coupled to processor 103.

Processor 103 may include any system, device, or apparatus configured to interpret and/or execute program instructions and/or process data, and may include, without limitation, a microprocessor, microcontroller, digital signal processor (DSP), application specific integrated circuit (ASIC), or any other digital or analog circuitry configured to interpret and/or execute program instructions and/or process data. In some embodiments, processor 103 may interpret and/or execute program instructions and/or process data stored in memory 104, and/or another component of information handling system 102.

Memory 104 may be communicatively coupled to processor 103 and may include any system, device, or apparatus configured to retain program instructions and/or data for a period of time (e.g., computer-readable media). Memory 104 may include random access memory (RAM), electrically erasable programmable read-only memory (EEPROM), a PCMCIA card, flash memory, magnetic storage, opto-magnetic storage, or any suitable selection and/or array of volatile or non-volatile memory that retains data after power to its associated information handling system 102 is turned off.

I/O interface 106 may comprise any suitable system, apparatus, or device operable to serve as an interface between information handling system 102 and one or more other external devices. For example, in some embodiments, I/O interface 106 may comprise a network interface configured to serve as an interface between information handling system 102 and other information handling systems via a network, in which case I/O interface 106 may comprise a network interface card, or "NIC."

User interface 110 may comprise any instrumentality or aggregation of instrumentalities by which a user may interact with information handling system 102. For example, user interface 110 may permit a user to input data and/or instructions into information handling system 102, and/or otherwise manipulate information handling system 102 and its associated components. User interface 110 may also permit information handling system 102 to communicate data to a user, e.g., by way of a display device.

Network port 112 may comprise an electrical connector in the form of any suitable combination of a jack, a socket, and/or a "cage" for receiving a corresponding connector of a cable. For example, in some embodiments, such a connector may include an 8 position 8 contact (8P8C) cable termination of a Category 5 or a Category 6 cable. As another example, such a connector may include a multi-fiber push on (MPO) cable termination of a fiber optical cable. These enumerated examples are not intended to be limiting, and network port 112 may be configured to receive any suitable type of connector for terminating any suitable type of cable.

Air mover assembly 114 may include any suitable system, device, or apparatus comprising an air mover 108 and associated components (e.g., housing, electronic components for controlling and/or monitoring operation of air mover 108, etc.). In some embodiments, air mover assembly 114 may comprise a modular assembly that may be readily inserted into and readily removed from a corresponding air mover bay formed within an enclosure of information handling system 102. As shown in FIG. 1, air mover assembly 114 may include an air mover 108, a particle sensor 116, a gas sensor 118, and a visual indicator 120.

Air mover 108 may include any mechanical, electrical, or electro-mechanical system, apparatus, or device operable to move air and/or other gases in order to cool information handling resources of information handling system 102. In some embodiments, air mover 108 may comprise a fan (e.g., a rotating arrangement of vanes or blades which act on the air). In other embodiments, air mover 108 may comprise a blower (e.g., a centrifugal fan that employs rotating impellers to accelerate air received at its intake and change the direction of the airflow). In these and other embodiments, rotating and other moving components of air mover 108 may be driven by a motor.

Particle sensor 116 may comprise any system, device, or apparatus configured to detect the presence of particulate matter (e.g., dust, metal shavings, etc.) at or on particle sensor 116. In some embodiments, particle sensor 116 may be configured to detect a particular type or particular types of particulate matter. In operation, particle sensor 116 may be configured such that the presence of particulate matter on a sensing component of particle sensor 116 may alter a physical property (e.g., an electrical impedance) of such sensing component. In response to a change in such physical property beyond a threshold amount, particle sensor 116 may communicate a signal to processor 103 and/or visual indicator 120 indicating such change.

Gas sensor 118 may comprise any system, device, or apparatus configured to detect the presence of one or more particular gases (e.g., sulfur, nitrogen, etc.) at or on gas sensor 118. In operation, gas sensor 118 may be configured such that the presence of a particular gas on a sensing component of gas sensor 118 may alter a physical property (e.g., an electrical impedance) of such sensing component. In response to a change in such physical property beyond a threshold amount, gas sensor 118 may communicate a signal to processor 103 and/or visual indicator 120 indicating such change.

Visual indicator 120 may comprise any system, device, or apparatus configured to, in response to one or more control signals communicated to visual indicator 120 indicative of an occurrence of an event, generate a human-perceptible visual indication of the occurrence of the event. For example, in some embodiments, visual indicator 120 may include a light-emitting diode.

In some embodiments, particle sensor 116 and gas sensor 118 may reside within the airflow path driven by air mover 108. Accordingly, in operation, particle sensor 116 and gas sensor 118 may be able to detect the presence of particles and/or gases that may be harmful to printed circuit boards, ports, and/or other components of information handling system 102. Further, in the presence of such potentially harmful particles and/or gases, particle sensor 116 and/or gas sensor 118 may communicate a signal to visual indicator 120 and/or processor 103 (and processor 103 may in turn communicate an alert to user interface 110), thus alerting a person (e.g., administrator, technician, end user, etc.) to the presence of harmful particles and/or gases such that the person may take remedial action to mitigate the presence of such harmful particles and/or gases.

In addition to processor 103, memory 104, I/O interface 106, user interface 110, network port 112, and air mover assembly 114, information handling system 102 may include one or more other information handling resources. Such an information handling resource may include any component, system, device, or apparatus of an information handling system, including without limitation, a processor, bus, memory, I/O device and/or interface, storage resource (e.g., hard disk drives), network interface, electro-mechanical device (e.g., fan), display, power supply, and/or any portion thereof. An information handling resource may comprise any suitable package or form factor, including without limitation an integrated circuit package or a printed circuit board having mounted thereon one or more integrated circuits.

FIG. 2A illustrates a perspective view of selected components of an example air mover assembly 114A, in accordance with embodiments of the present disclosure. In some embodiments, air mover assembly 114A depicted in FIG. 2A may be used to implement air mover assembly 114 depicted in FIG. 1. As shown in FIG. 2A, air mover assembly 114A may include a housing 202A configured to house an air mover 108A (which may be used to implement air mover 108) and a printed circuit board 204A.

Printed circuit board 204A may have mounted thereto a plurality of electronic components for controlling and/or monitoring operation of air mover 108A. In addition, printed circuit board 204A may have mounted thereto particle sensor 116A (which may be used to implement particle sensor 116) and gas sensor 118A (which may be used to implement gas sensor 118), such that particle sensor 116A and gas sensor 118A are within the airflow driven by air mover 108A, thus allowing particle sensor 116A and gas sensor 118A to detect potentially harmful particles and/or gases present in the airflow.

FIG. 2B illustrates a perspective view of selected components of another example air mover assembly 114B, in accordance with embodiments of the present disclosure. In some embodiments, air mover assembly 114B depicted in FIG. 2B may be used to implement air mover assembly 114 depicted in FIG. 1. As shown in FIG. 2B, air mover assembly 114B may include a housing 202B configured to house an air mover 108B (which may be used to implement air mover 108) and a printed circuit board 204B.

Printed circuit board 204B may have mounted thereto a plurality of electronic components for controlling and/or monitoring operation of air mover 108B. In addition, printed circuit board 204B may have mounted thereto particle sensor 116B (which may be used to implement particle sensor 116) and gas sensor 118B (which may be used to implement gas sensor 118), such that particle sensor 116B and gas sensor 118B are within the airflow driven by air mover 108B, thus allowing particle sensor 116B and gas sensor 118B to detect potentially harmful particles and/or gases present in the airflow.

As used herein, when two or more elements are referred to as "coupled" to one another, such term indicates that such two or more elements are in electronic communication or mechanical communication, as applicable, whether connected indirectly or directly, with or without intervening elements.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative. Accordingly, modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

Although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described above.

Unless otherwise specifically noted, articles depicted in the drawings are not necessarily drawn to scale.

All examples and conditional language recited herein are intended for pedagogical objects to aid the reader in understanding the disclosure and the concepts contributed by the inventor to furthering the art, and are construed as being without limitation to such specifically recited examples and conditions. Although embodiments of the present disclosure have been described in detail, it should be understood that various changes, substitutions, and alterations could be made hereto without departing from the spirit and scope of the disclosure.

Although specific advantages have been enumerated above, various embodiments may include some, none, or all of the enumerated advantages. Additionally, other technical advantages may become readily apparent to one of ordinary skill in the art after review of the foregoing figures and description.

To aid the Patent Office and any readers of any patent issued on this application in interpreting the claims appended hereto, applicants wish to note that they do not intend any of the appended claims or claim elements to invoke 35 U.S.C. § 112(f) unless the words "means for" or "step for" are explicitly used in the particular claim.

What is claimed is:

1. An information handling system comprising:
   a chassis configured to house components of the information handling system; and
   an air mover assembly comprising:
      an enclosure;
      an air mover within the enclosure configured to drive airflow to cool one or more components of the information handling system;
      a printed circuit board fastened to the enclosure, positioned within the airflow driven by the air mover, and communicatively coupled to the air mover, wherein components mounted on the printed circuit board include:
         components for controlling operation of the air mover; and
         a harmful matter sensor configured to detect a presence of matter harmful to one or more components of the information handling system.

2. The information handling system of claim 1, wherein the harmful matter sensor comprises a particle sensor configured to detect the presence of particulate matter harmful to one or more components of the information handling system.

3. The information handling system of claim 1, wherein the harmful matter sensor comprises a gas sensor configured to detect the presence of a gas harmful to one or more components of the information handling system.

4. The information handling system of claim 1, wherein the printed circuit board includes first and second substantially planar major surfaces and wherein the printed circuit board is affixed to the housing with the first and second substantially planar surfaces oriented in parallel with the air flow driven by the air mover.

5. The information handling system of claim 1, wherein the air mover assembly is configured to be readily removable from the chassis.

6. An air mover assembly comprising:
   an enclosure;
   an air mover within the enclosure configured to drive airflow to cool one or more components of an information handling system comprising the air mover assembly;
   a printed circuit board affixed to the enclosure, positioned within the airflow driven by the air mover, and communicatively coupled to the air mover, wherein components mounted on the printed circuit board include:
      components for controlling operation of the air mover; and
      a harmful matter sensor configured to detect a presence of matter harmful to one or more components of the information handling system.

7. The air mover assembly of claim 6, wherein the harmful matter sensor comprises a particle sensor configured to detect the presence of particulate matter harmful to one or more components of the information handling system.

8. The air mover assembly of claim 6, wherein the harmful matter sensor comprises a gas sensor configured to detect the presence of a gas harmful to one or more components of the information handling system.

9. The air mover assembly of claim 6, wherein:
   the air mover assembly further comprises a printed circuit board communicatively coupled to the air mover and comprising components for control or monitoring of operation of the air mover; and
   the harmful matter sensor is mounted on the printed circuit board.

10. The air mover assembly of claim 6, wherein the air mover module is configured to be readily removable from the chassis.

11. A method comprising:
    housing an air mover within an enclosure of an air mover assembly, wherein the air mover is configured to drive airflow to cool one or more components of an information handling system comprising the air mover assembly; and
    fastening, to the enclosure, a printed circuit board positioned within the airflow driven by the air mover, wherein components mounted on the printed circuit board include:
       components for controlling operation of the air mover; and
       a harmful matter sensor configured to detect a presence of matter harmful to one or more components of the information handling system.

12. The method of claim 11, wherein the harmful matter sensor comprises a particle sensor configured to detect the presence of particulate matter harmful to one or more components of the information handling system.

13. The method of claim 11, wherein the harmful matter sensor comprises a gas sensor configured to detect the presence of a gas harmful to one or more components of the information handling system.

14. The method of claim 11, wherein the printed circuit board includes first and second substantially planar major surfaces and wherein the printed circuit board is affixed to the housing with the first and second substantially planar surfaces oriented in parallel with the air flow driven by the air mover.

15. The method of claim 11, wherein the air mover assembly is configured to be readily removable from the chassis.

\* \* \* \* \*